US011345756B2

(12) United States Patent
Ambati

(10) Patent No.: US 11,345,756 B2
(45) Date of Patent: *May 31, 2022

(54) CCR3 INHIBITION FOR OCULAR ANGIOGENESIS AND MACULAR DEGENERATION

(71) Applicant: University of Kentucky Research Foundation, Lexington, KY (US)

(72) Inventor: Jayakrishna Ambati, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 139 days.

This patent is subject to a terminal disclaimer.

(21) Appl. No.: 16/425,293

(22) Filed: May 29, 2019

(65) Prior Publication Data

US 2019/0276545 A1 Sep. 12, 2019

Related U.S. Application Data

(62) Division of application No. 11/357,288, filed on Feb. 16, 2006, now Pat. No. 10,344,095.

(51) Int. Cl.
*C07K 16/28* (2006.01)
*C07K 16/24* (2006.01)
*A61K 31/445* (2006.01)
*A61K 38/00* (2006.01)

(52) U.S. Cl.
CPC ........ *C07K 16/2866* (2013.01); *A61K 31/445* (2013.01); *C07K 16/24* (2013.01); *A61K 38/00* (2013.01); *C07K 2317/73* (2013.01); *C07K 2317/76* (2013.01)

(58) Field of Classification Search
CPC ...................................................... A61P 27/02
See application file for complete search history.

(56) References Cited

U.S. PATENT DOCUMENTS

| 6,566,376 B1 * | 5/2003 | Baxter .................... A61P 11/00 514/326 |
| 8,592,482 B2 * | 11/2013 | Ambati .................. A61K 38/02 514/562 |
| 8,778,616 B2 * | 7/2014 | Ambati .................... A61P 27/02 435/7.1 |
| 2004/0082790 A1 * | 4/2004 | Duncia .................... A61P 11/00 546/246 |
| 2004/0234505 A1 | 11/2004 | Naylor et al. |

OTHER PUBLICATIONS

Nakamura et al. Immunologic Research, Dec. 2005, vol. 33, No. 3, pp. 213-221 (Year: 2005).*
Aird, W.C., "Mechanisms of endothelial cell heterogeneity in health and disease", Circ Res 2006, 98:159-162.
Danesi R. et al. "Suramin inhibits bFGF-induced endothelial cell proliferation and angiogenesis in the chick chorioallantoic membrane" Br J Cancer. (1993); 68: 932-938).
Hendricks, J. et al., "Molecular diversity of cardiac endothelial cells in vitro and in vivo", Physiol Genomics 2004, 19:198-206.
Hwang et al., FEBS Letters, 2004, 570:47-51.
Kimura et al. "A new model of subretinal neovascularization in the rabbit" Invest Ophthalmol Vis Sci (1995) 36:2110-2119.
Lang, I. et al., "Differential mitogenic responses of human macrovascular and microvascular endothelial cells to cytokines underline their phenotypic heterogeneity", Cell Prolif 2001, 34:143-155.
Langenkamp et al., "Microvascular endothelial cell heterogeneity: general concepts and pharmacological consequences for anti-agiogenic therapy of cancer" Cell Tissue Res 335:205-222 (2009).
Mason, J.C. et al., "Human umbilical vein and dermal microvascular endothelial cells show heterogeneity in response to PKC activation", Am J Physiol Cell Physiol, 1997, 273:1233-1240.
Oh, P et al., "Subtractive proteomic mapping of the endothelial surface in lung and solid tumours for tissue-specific therapy", Nature 2004, 429:629-635.
Sakamoto T. et al. "Effect of tecogalan sodium on angiogenesis in vitro by choroidal endothelial cells" Investigative Ophthalmology & Visual Science. (1995): 36:1076-1083, 1995).
Salcedo et al., J. Immunol. 2001, 166:7571-7578.
Sheikine et al. Atherosclerosis 2006 189:458-463.
Shin, D. and Anderson, D.J., "Isolation of arterial-specific genes by subtractive hybridization reveals molecular heterogeneity among arterial endothelial cells", Developmental Dynamics, 2005, 233:1589-1604.
Smith, J.R. et al., "Unique gene expression profiles of donor-matched human retinal and choroidal vascular endothelial cells", Investigative Ophtal & Visual Sci 2007, Vo. 48, No. 6, pp. 2676-2684.
Soubrane et al., "Basic fibroblast growth factor experimentally induced choroidal angiogenesis in the minipig" Curr Eye Res (1994) 13:183-195).
St. Croix, B. et al., "Genes Expressed in Human Tumor Endothelium," Sci 2000, 289, 1197.
Thorin, E. and Shreeve, S.M., "Heterogeneity of vascular endothelial cells in normal and disease states", Pharmacol Ther 1998, vol. 78, No. 3, pp. 115-156.
Tigges U. et al. "FGF2-dependent neovascularization of subcutaneous Matrigel plugs is initiated by bone marrow-derived pericytes and macrophages" Development (2008); 135: 523-532).
Tobe et al. "Targeted Disruption of the FGF2 Gene Does Not Prevent Choroidal Neovascularization in a Murine Model" American Journal of Pathology (1998) 153:1641-1646.
Troy Stevens "Molecular and Cellular Determinants of Lung Endothelial Cell Heterogeneity" Chest 128: 558S-564S (2005).

(Continued)

*Primary Examiner* — James D. Anderson
(74) *Attorney, Agent, or Firm* — Crowell & Moring LLP

(57) ABSTRACT

Provided are methods and compositions for the treatment or prevention of ocular angiogenesis and neovascularization. Administration of inhibitors of the CCR3 receptor or its ligands eotaxin (CCL11), eotaxin-2 (CCL24) or eotaxin-3 (CCL26) inhibits ocular angiogenesis.

12 Claims, 5 Drawing Sheets

(56) References Cited

OTHER PUBLICATIONS

Yashima, R. et al., "Heterogeneity of the signal transduction pathways for VEGF-induced MAPKs activation in human vascular endothelial cells," J Cell Physiol 2001, 188:201-210.
Zamora, D.O. et al., Proteomic profiling of human retinal and choroidal endothelial cells reveals molecular heterogeneity related to tissue of origin, Molecular Vision 2007, 13:2058-65.
Zhang et al., "In vivo differences between endothelial transcriptional profiles of coronary and iliac arteries revealed by micro array analysis" American J Physiol Heart Circ. Physiol 295:H1556-H1561 (2008).
Salcedo et al., The Journal of Immunology, 2001, 166:7571-7578.
Wallace et al., Prog. Retin Eye Res. 2004, 23 :435-448.
Wallace et al., "The role of chemokines and their receptors in ocular disease," Prog. Retin. Eye Res. 2004, 23:435-448.

\* cited by examiner

CCR3 INHIBITION FOR OCULAR ANGIOGENESIS AND MACULAR DEGENERATION

CROSS REFERENCE TO RELATED APPLICATIONS

This application is a Divisional of U.S. application Ser. No. 11/357,288, filed Feb. 16, 2006, the disclosures of which are expressly incorporated by reference herein.

FIELD OF THE INVENTION

The present invention relates to the suppression of ocular angiogenesis by inhibiting the CCR3 receptor.

DESCRIPTION OF THE RELATED ART

The macula is the part of the retina which is responsible for central vision. Age-related macular degeneration is a chronic eye disease that occurs when tissue in the macula deteriorates. Macular affects central vision, but not peripheral vision. Macular degeneration is the leading cause of severe vision loss in people age 60 and older.

There are two forms of age-related macular degeneration: dry and wet. Dry macular degeneration is the most common type of macular degeneration and occurs when cells of the macula slowly begin to break down. Yellow deposits called "drusen" form under the retina between the retinal pigmented epithelium (RPE) and Bruch's membrane, which supports the retina. The drusen deposits are debris associated with compromised cell metabolism in the RPE. Eventually there is a deterioration of the macular regions associated with the drusen deposits resulting in a loss of central vision.

Wet macular degeneration occurs when abnormal bold vessels grow behind the macula. These vessels are fragile and can leak fluid and blood, which result in scarring of the macula and raise the potential for rapid, severe damage. Bruch's membrane breaks down, usually near drusen deposits. This is where new blood vessel growth, or neovascularization, occurs. Central vision can become distorted or lost entirely in a short period of time, sometimes within days. Wet macular degeneration is responsible for about 10 percent of the cases of age-related macular degeneration, but it accounts for about 90 percent of the cases of legal blindness.

SUMMARY OF THE INVENTION

The present invention relates to a method of inhibiting ocular angiogenesis. The method comprises exposing a choroidal cell to a CCR3-inhibitory effective amount of a compound which inhibits the activity of CCR3. The present invention also relates to a composition for the inhibition of ocular angiogenesis. The composition comprises a compound which inhibits the activity of CCR3.

Other systems, methods, features and advantages of the present invention will be or become apparent to one with skill in the art upon examination of the following drawings and detailed description. It is intended that all such additional systems, methods, features and advantages be included within this description, be within the scope of the present invention, and be protected by the accompanying claims.

DESCRIPTION OF PREFERRED EMBODIMENTS

Figure 1:
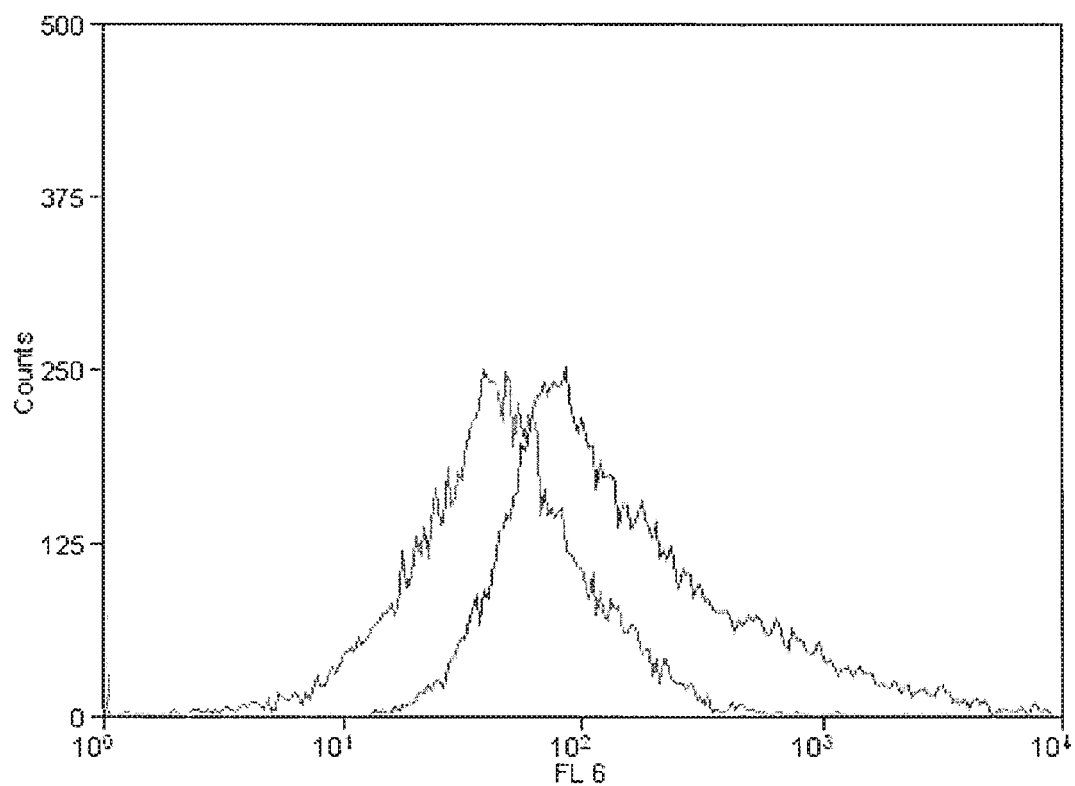
FIG. 1 illustrates the effect of laser injury on the number of CCR3 receptors on choroidal endothelial cells.

Intraocular inflammation is not clinically apparent in age-related macular degeneration. However, there is evidence suggesting an influential role for inflammation in this condition. CCR3 is a promiscuous chemokine receptor that is predominantly expressed by eosinophils but also is found on other leukocytes and some endothelial and epithelial cells.

The invention relates to methods and compositions for the treatment or prevention of ocular angiogenesis and neovascularization. Administration of inhibitors of the CCR3 receptor or its ligands, for example eotaxin (CCL11), eotaxin-2 (CCL24) or eotaxin-3 (CCL26), inhibits ocular angiogenesis. Ocular angiogenesis includes choroidal angiogenesis and retinal angiogenesis. Compositions and methods for inhibiting CCR3, eotaxin (CCL11), eotaxin-2 (CCL24), and eotaxin-3 (CCL26) for the treatment and/or prevention of neovascular disease are provided. Also provided are novel therapeutic targets and diagnostic markers for choroidal neovascularization.

Any compound which inhibits the activity of CCR3 may be used in the present invention. Such compounds include inhibitory molecules which bind directly to the CCR3 receptor, antibodies which bind the CCR3 receptor or to the natural ligands of the CCR3 receptor, including eotaxin (CCL11), eotaxin-2 (CCL24) and eotaxin-3 (CCL26), RNA, DNA or RNA/DNA aptamers which specifically bind CCR3, eotaxin, eotaxin-2 or eotaxin-3, and siRNA or anti-sense oligonucleotides which inhibit the expression of CCR3, eotaxin, eotaxin-2 or eotaxin-3.

Numerous "small molecule" inhibitors for the CCR3 receptor have been developed and can be used in the present invention. In one aspect the CCR3 inhibitor is an organic molecule having a molecular weight less than 1000. In another aspect of the invention, the CCR3 inhibitor is an organic molecule having a molecular weight less than 500. The CCR3 receptor inhibitors include piperidine derivatives, piperidine amides and biperidine compounds such as those described in U.S. Pat. Nos. 6,984,651 and 6,903,115, and U.S. published applications 20050176708, 20050182094 and 20050182095; heterocyclic piperidines such as those described in U.S. Pat. No. 6,759,411; diphenyl-piperidine derivatives such as those described in U.S. Pat. No. 6,566,376; 2,5-substituted pyrimidine derivatives such as those described in U.S. Pat. No. 6,984,643; piperizinones such as those described in U.S. Pat. No. 6,974,869; bicycylic and tricyclic amines such as those described in U.S. Pat. No. 6,960,666; N-ureidoalkyl-piperidines such as those described in U.S. Pat. Nos. 6,949,546, 6,919,368, 6,906,066, 6,897,234, 6,875,776, 6,780,857, 6,627,629, 6,521,592 and 6,331,541; bicyclic diamines such as those described in U.S. Pat. No. 6,821,964; benzylcycloalkyl amines such as those described in U.S. Pat. No. 6,864,380; 2-substituted-4-nitrogen heterocycles such as those described in U.S. Pat. No. 6,706,735; ureido derivatives of poly-4-amino-2-carboxy-1- methyl pyrrole compounds; bicyclic and bridged nitrogen heterocycles such as those described in U.S. published application 20050234034; azetidine derivatives such as those described in U.S. published application 20050222118; substituted fused bicyclic amines such as those described in U.S. published application 20050197373; substituted spiro azabicyclics such as those described in U.S. published application 20050197325; piperidine-substituted indoles or heteroderivatives thereof such as those described in U.S. published application 20050153979; piperidinyl and piperazinyl compounds substituted with bicyclo-heterocyclylalkyl groups such as those described in U.S. published application 20050090504; arylsulfonamide derivatives such as those described in U.S. published application 20050070582; 1-phenyl-1,2-diaminoethane derivatives such as those described in U.S. published application 20040063779; (N-{[2S]-4-(3,4-dichlorobenzyl)morpholin-2-yl}methyl)-N' [(2-methyl-2H-tetraazol-5-yl)methyl]urea) (see, e.g., Nakamura et al., Immunol Res., 33:213-222, 2006; N-{(3R)-1-[(6-fluoro-2-naphthyl)methyl]pyrrolidin-3-yl}-2-{1-[(3-methyl-1-oxidopyridin-2-yl)carbonyl]piperidin-4-ylidene}acetamide (see, e.g., Suzuki et al., Biochem. Biophys. Res. Commun., 339:1217-1223, 2006; N-{(3R)-1-[(6-fluoro-2-naphthyl)methyl]pyrrolidin-3-yl}-2-{1-[(5-hydroxy-3-methylpyridin-2-yl)carbonyl]piperidin-4-ylidene}acetamide hemifumarate (see, e.g., Morokata et al., J. Pharmacol. Exp. Ther., Dec. 9, 2005 [Epub ahead of print]); bipiperidine amide antagonists of CCR3 such as those described in Ting et al., Bioorg. Med. Chem. Lett., 15:3020-3023, 2005; (S)-methyl-2-naphthoylamino-3-(4-nitrophenyl)propionate (see, e.g., Beasley et al., J. Allergy Clin. Immunol., 105: S466-S472, 2000; and the CCR3 antagonist compounds described in Fryer et al., J. Clin. Invest., 116:228-236, 2006.

Additional compounds for inhibiting the CCR3 receptor include RNA, DNA or RNA/DNA aptamers directed against CCR3, eotaxin, eotaxin-2 or eotaxin-3. Exemplary methods for making aptamers are described in U.S. Pat. Nos. 5,270,163, 5,840,867, 6,180,348 and 6,699,843.

Additional compounds for inhibiting the CCR3 receptor include anti-sense oligonucleotides or siRNAs directed against CCR3, eotaxin, eotaxin-2 or eotaxin-3, including the anti-sense oligonucleotides directed against the CCR3 receptor such as that described in U.S. Pat. No. 6,822,087.

The siRNAs for use in the present invention are designed according to standard methods in the field of RNA interference. Introduction of siRNAs into cells may be by transfection with expression vectors, by transfection with synthetic dsRNA, or by any other appropriate method. Transfection with expression vectors is preferred.

The expression vectors which can be used to deliver siRNA according to the invention include retroviral, adenoviral and lentiviral vectors. The expression vector includes a sequence which codes for a portion of the target gene (e.g., CCR3 receptor, eotaxin, eotaxin-2 or eotaxin-3) which is to be silenced. The target gene sequence is designed such that, upon transcription in the transfected host, the target RNA sequence forms a hairpin structure due to the presence of self-complementary bases. Processing within the cell removes the loop resulting in formation of a siRNA duplex. The double stranded RNA sequence should be less than 30 nucleotide bases; preferably the dsRNA sequence is 19-25 bases in length; more preferably the dsRNA sequence is 20 nucleotides in length.

The expression vectors may include one or more promoter regions to enhance synthesis of the target gene sequence. Promoters which can be used include CMV promoter, SV40 promoter, promoter of mouse U6 gene, and promoter of human H1 gene.

One or more selection markers may be included to facilitate transfection with the expression vector. The selection marker may be included within the expression vector, or may be introduced on a separate genetic element. For example, the bacterial hygromycin B phosphotransferase gene may be used as a selection marker, with cells being grown in the presence of hygromycin to select for those cells transfected with the aforementioned gene.

Synthetic dsRNA may also be introduced into cells to provide gene silencing by siRNA. The synthetic dsRNAs are less than 30 base pairs in length. Preferably the synthetic dsRNAs are 19-25 base pairs in length. More preferably the dsRNAs are 19, 20 or 21 base pairs in length, optionally with 2-nucleotide 3' overhangs. The 3' overhangs are preferably TT residues.

Synthetic dsRNAs can be introduced into cells by injection, by complexing with agents such as cationic lipids, by use of a gene gun, or by any other appropriate method.

Additional compounds for inhibiting the CCR3 receptor include antibodies which specifically bind the CCR3 receptor, eotaxin, eotaxin-2 or eotaxin-3. Exemplary antibodies which specifically bind and inhibit the CCR3 receptor are described in U.S. Pat. Nos. 6,806,061 and 6,207,155, and in U.S. published applications 20050191702, 20050069955, and 20020147312. Exemplary antibodies which specifically bind and inhibit eotaxin and eotaxin-2 are described in U.S. Pat. Nos. 6,946,546 and 6,635,251, and in U.S. published applications 20040191255 and 20040014132.

The antibodies of the present invention can be polyclonal or monoclonal, and the term antibody is intended to encompass both polyclonal and monoclonal antibodies. Antibodies of the present invention can be raised against an appropriate immunogen, including proteins or polypeptides of the present invention, such as isolated and/or recombinant mammalian CCR3 receptor, eotaxin, eotaxin-2 or eotaxin-3 protein or portion thereof, or synthetic molecules, such as synthetic peptides.

Preparation of immunizing antigen, and polyclonal and monoclonal antibody production can be performed using any suitable technique. A variety of methods have been described (see e.g., Kohler et al., Nature, 256: 495-497 (1975) and Eur. J. Immunol. 6: 511-519 (1976); Milstein et al., Nature 266: 550-552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0) with antibody producing cells. The antibody producing cell, preferably those of the spleen or lymph nodes, are obtained from animals immunized with the antigen of interest. The fused cells (hybridomas) are isolated using selective culture conditions, and cloned by limiting dilution. Cells which produce antibodies with the desired specificity are selected by a suitable assay (e.g., ELISA).

Single chain antibodies, and chimeric, humanized or primatized (CDR-grafted) antibodies, as well as chimeric or CDR-grafted single chain antibodies, comprising portions derived from different species, are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023. B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single chain antibodies.

In addition, functional fragments of antibodies, including fragments of chimeric, humanized, primatized or single chain antibodies, can also be produced. Functional fragments of foregoing antibodies retain at least one binding function and/or modulation function of the full-length antibody from which they are derived. For example, antibody fragments capable of binding to a mammalian CCR3 receptor, eotaxin, eotaxin-2 or eotaxin-3 or portion thereof, including, but not limited to, Fv, Fab, Fab' and F(ab').sub.2 fragments are encompassed by the invention. Such fragments can be produced by enzymatic cleavage or by recombinant techniques. For instance, papain or pepsin cleavage can generate Fab or F(ab').sub.2 fragments, respectively. Alternatively, antibodies can be produced in a variety of truncated forms using antibody genes in which one or more stop codons has been introduced upstream of the natural stop site. For example, a chimeric gene encoding a F(ab').sub.2 heavy chain portion can be designed to include DNA sequences encoding the CH.sub.1 domain and hinge region of the heavy chain.

The antibodies of the present invention can be used to modulate receptor or ligand function in research and therapeutic applications. For instance, antibodies can act as inhibitors to inhibit (reduce or prevent) (a) binding (e.g., of a ligand, a second inhibitor or a promoter) to the receptor, (b) a receptor signalling, (c) and/or a stimulatory function. Antibodies which act as inhibitors of receptor function can block ligand or promoter binding directly or indirectly (e.g., by causing a conformational change). For example, antibodies can inhibit receptor function by inhibiting binding of a ligand, or by desensitization (with or without inhibition of binding of a ligand).

Anti-idiotypic antibodies are also provided. Anti-idiotypic antibodies recognize antigenic determinants associated with the antigen-binding site of another antibody. Anti-idiotypic antibodies can be prepared against a second antibody by immunizing an animal of the same species, and preferably of the same strain, as the animal used to produce the second antibody. See e.g., U.S. Pat. No. 4,699,880. Single chain, and chimeric, humanized or primatized (CDR-grafted), as well as chimeric or CDR-grafted single chain anti-idiotypic antibodies can be prepared, and are encompassed by the term anti-idiotypic antibody. Antibody fragments of such antibodies can also be prepared.

Modulation of mammalian CCR3 receptor function according to the present invention, through the inhibition of at least one function characteristic of a mammalian CCR3 receptor, provides an effective and selective way of inhibiting ocular angiogenesis. One or more inhibitors of CCR3 receptor function, such as those identified as described herein, can be used to inhibit ocular angiogenesis for therapeutic purposes.

Thus, the present invention provides a method of inhibiting ocular angiogenesis in an individual in need of such therapy, comprising administering a compound which inhibits mammalian CCR3 receptor function to an individual in need of such therapy. Such individuals include those having age-related macular degeneration.

The methods of the present invention can be used in any mammalian species, including human, monkey, cow, sheep, pig, goat, horse, mouse, rat, dog, cat, rabbit, guinea pig, hamster and horse. Humans are preferred.

According to the method of the invention, one or more compounds can be administered to the host by an appropriate route, either alone or in combination with another drug. An effective amount of a compound (e.g., a small molecule CCR3 receptor antagonist which inhibits ligand binding, an antibody or an siRNA) is administered. An effective amount is an amount sufficient to achieve the desired therapeutic effect, under the conditions of administration, such as an amount sufficient for inhibition of a CCR3 receptor function, and thereby inhibition of ocular angiogenesis.

A variety of routes of administration are possible including, but not necessarily limited to oral, dietary, topical, parenteral (e.g., intravenous, intraarterial, intramuscular, subcutaneous injection), inhalation (e.g., intrabronchial, intranasal or oral inhalation, intranasal drops), and intraocular injection routes of administration, depending on the disease or condition to be treated. Intraocular injection routes include periocular (subconjunctival/transscleral), intravitreous, subretinal and intracameral modes of injection.

Formulation of a compound to be administered will vary according to the route of administration selected (e.g., solution, emulsion, capsule). An appropriate composition comprising the compound to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, Remington's Pharmaceutical Science, 16th Edition, Mack, Ed. 1980). For inhalation, the compound is solubilized and loaded into a suitable dispenser for administration (e.g., an atomizer, nebulizer or pressurized aerosol dispenser).

Example 1

Methods

Laser photocoagulation (532 nm, 200 mW, 100 ms, 75 μm) (OCULIGHT™ GL, Index Corporation) was performed (volume studies: 3/eye; protein analyses/flow cytometry: 12/eye) on both eyes of each animal to induce CNV (choroidal neovascularization). CNV volumes were measured by scanning laser confocal microscope (TCS SP, Leica) with 0.5% FITC-*Griffonia simplicifolia* Isolectin B4 (Vector Laboratories). CNV was induced by laser injury in C57BL/6J and Ccr3$^{-/-}$ mice and volumes measured 7 days later by confocal evaluation of *Griffonia simplicifolia* Isolectin B4 staining of RPE-choroid flatmounts. Neutralizing antibodies (Ab) against CCR3, eotaxin (CCL-11), eotaxin-2 (CCL-24), RANTES, MCP-3 or control goat IgG or rat IgG$_{2a}$ were injected into the vitreous humor following injury.

Flow cytometry was used to determine the numbers of eosinophils, mast cells and macrophages in the choroid, expression of CCR3 by various cell types in the eye, and the cell cycle state of choroidal endothelial cells (CECs) in vivo.

Suspensions of cells isolated from mouse RPE/choroid by incubation with collagenase D (20 U/ml; Roche Diagnostics) treatment were incubated in Fc block (0.5 mg/ml; BD Pharmingen) for 15 min. on ice. Rat antibody to mouse CCR3 (1:250; Santa Cruz) coupled with PE-donkey antibody to rat IgG (1:250; Jackson Immunoresearch) were used to quantify cell surface receptor expression on choroidal endothelial cells, defined by $CD31^+$ $VEGFR-2^+$ expression, gated by FITC-conjugated rat antibody to mouse CD31 (1:250; BD Biosciences) and PerCP-Cy5.5-conjugated rat antibody to mouse CD11b (1:50; BDBiosciences). Macrophages, neutrophils, eosinophils and mast cells were defined as $F4/80^+CD11c^-$, $Gr-1^+F4/80^-$, $CCR3^{hi}CD3^-CD1171^{int}CD49d^+$ and $CCR31^{int}CD3^-$ $CD117^{hi}CD49d^+$ cells, respectively. DNA content for cell cycle was analyzed after incubation with propidium iodide (0.05 mg/ml; Molecular Probes) containing 0.1% TRITON™ X-100 and RNase A (0.1 mg/ml; Roche).

Because the probability of each laser lesion developing CNV is influenced by the group to which it belongs, the mouse, the eye, and the laser spot, the mean lesion volumes were compared using a linear mixed model with a split plot repeated measures design. The whole plot factor was the genetic group to which the animal belonged while the split plot factor was the eye. Statistical significance was determined at the 0.05 level. Post hoc comparison of means was constructed with a Bonferroni adjustment for multiple comparisons.

Results

Figure 2:
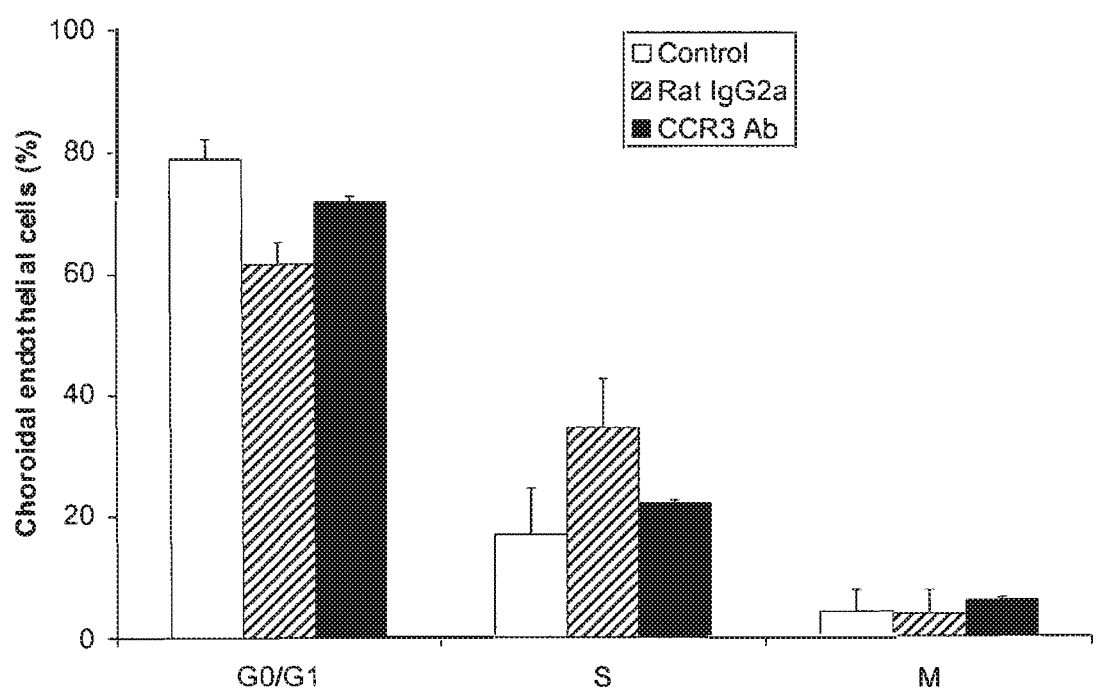
FIG. 2 shows the effect of CCR3 antibody on the proliferation of choroidal endothelial cells following laser injury.
Figure 3:
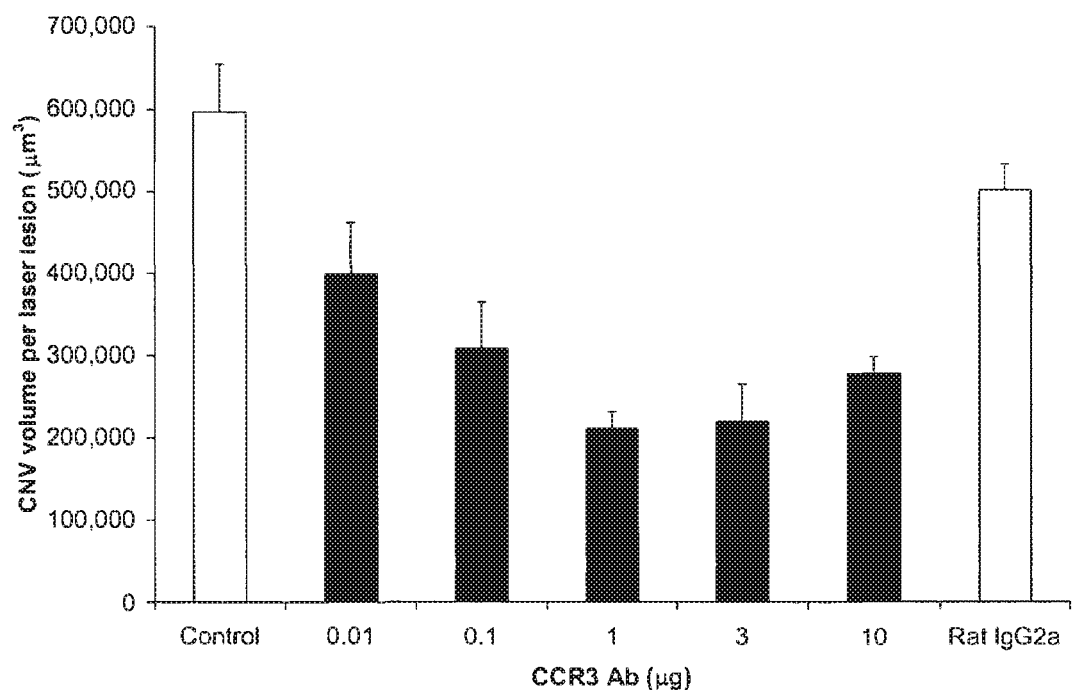
FIG. 3 illustrates the dose-dependent effect of CCR3 antibody on choroidal neovascularization volume
Figure 4:
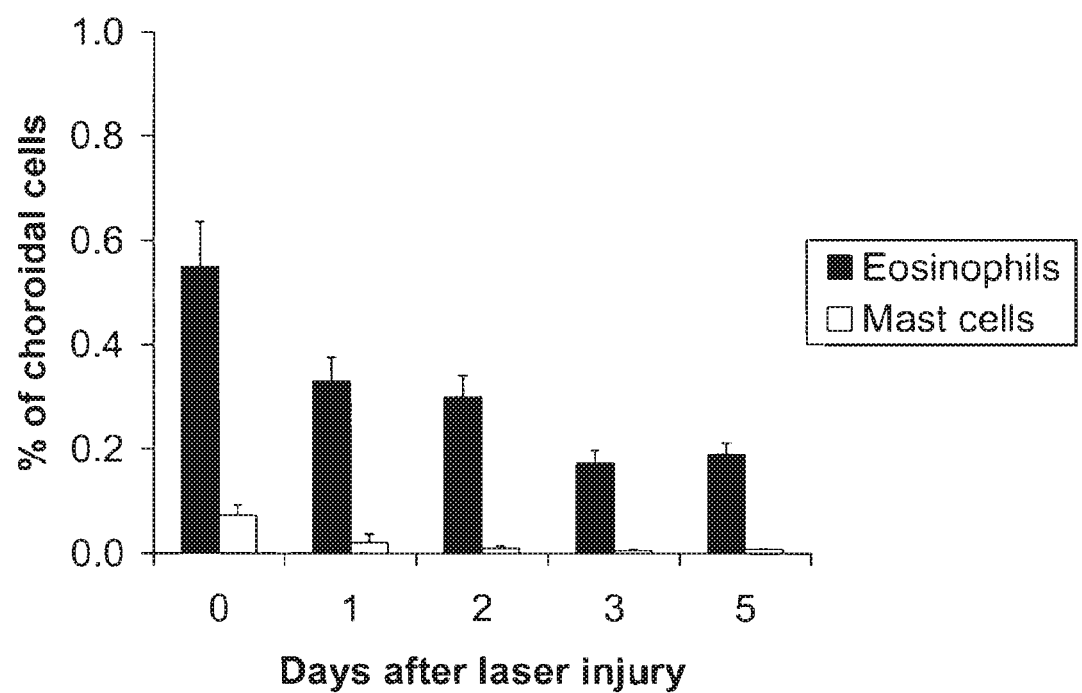
FIG. 4 shows lack of infiltration of eosinophils and mast cells into the choroid following laser injury.
Figure 5:
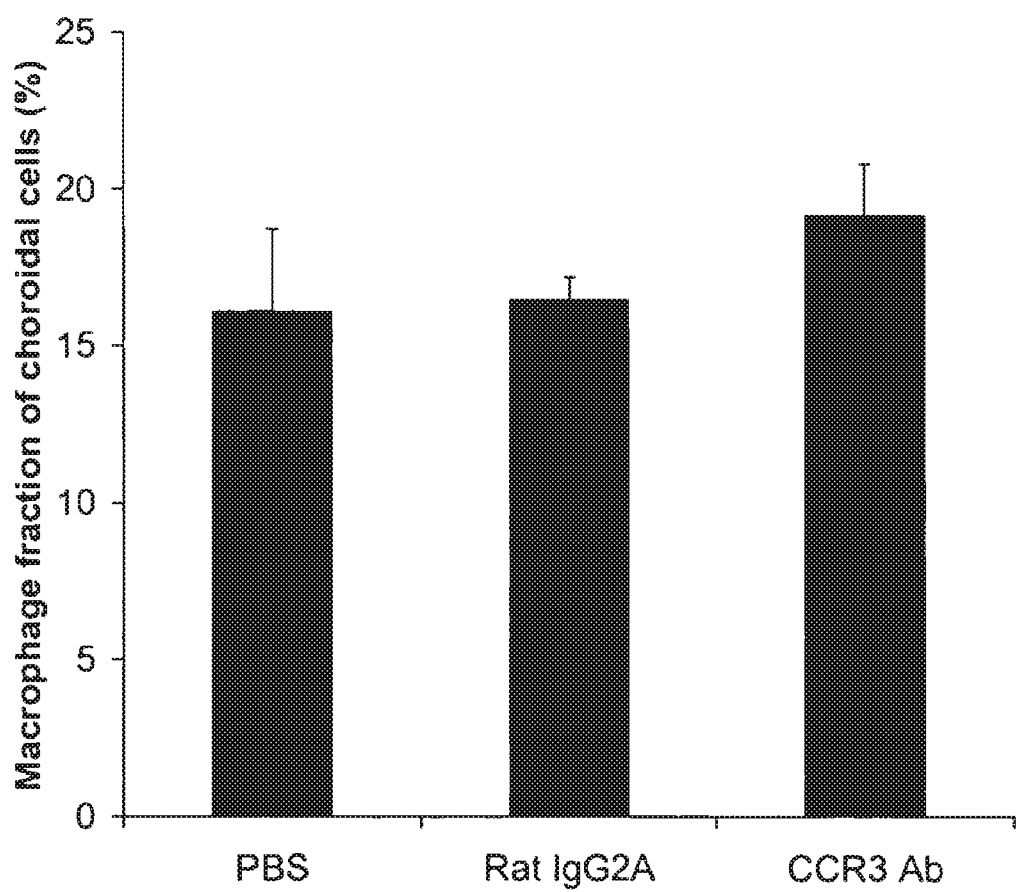
FIG. 5 illustrates the lack of change of number of infiltrating macrophages in the choroid following laser injury and CCR3 antibody treatment.

As illustrated by FIG. 1, the number of CCR3 receptors on choroidal endothelial cells in vivo following laser injury (red) is significantly greater than the number before injury (green), indicating upregulation of CCR3 receptors on these cells. Eosinophils or mast cells are the principal cells in most systems that respond to CCR3. However, the number of eosinophils and mast cells in the choroid was unaffected by injury or CCR3 Ab (FIG. 4). CCR3 Ab did not inhibit choroidal macrophage infiltration following injury (FIG. 5), indicating that laser injury is not working by anti-inflammatory means. As illustrated by FIG. 3, CCR3 Ab suppressed CNV volume in C57BL/6J mice by nearly 60% in a dose-dependent and statistically significant manner compared to vehicle control (PBS) and control antibody (rat IgG2a). FIG. 2 demonstrates that CCR3 Ab blockade, but not control antibody (rat IgG2a), inhibited proliferation (S phase) of CECs (choroidal endothelial cells) in vivo following laser injury. Experiments in $Ccr3^{-/-}$ mice confirmed these results. Of the CCR3 ligands, blockade of only eotaxin (45%) or eotaxin-2 (70%) suppressed CNV in C57BL/6J mice compared to control antibodies (all Ps<0.001). Experiments in $Ccl11^{-/-}$ and $Ccl24^{-/-}$ mice confirmed these results.

These findings demonstrate that CCR3 receptor promotes angiogenesis not via leukocyte modulation but rather by direct effects on CECs. Thus, CCL-11, CCL-24, and CCR3 are new targets for neovascular AMD (age-related macular degeneration).

All references cited in this disclosure are incorporated by reference to the same extent as if each reference had been incorporated by reference in its entirety individually.

While the invention has been described in detail and with reference to specific embodiments thereof, it will be apparent to one skilled in the art that various variations and modifications can be made therein without departing from the sprit and scope thereof. All such variations and modifications are intended to be included within the scope of this disclosure and the present invention and protected by the following claims.

I claim:

1. A method of treating ocular angiogenesis in a mammal in need of treatment for ocular angiogenesis comprising exposing a choroidal cell of the mammal to a CCR3-inhibitory effective amount of an organic molecule that inhibits the activity of CCR3, wherein ocular angiogenesis is treated in the mammal.

2. The method of claim 1, wherein the choroidal cell is a choroidal endothelial cell.

3. The method of claim 1, wherein the organic molecule is orally administered to the mammal.

4. The method of claim 1, wherein the organic molecule is intravenously administered to the mammal.

5. The method of claim 1, wherein the organic molecule is intraocularly injected into the mammal.

6. The method of claim 1, wherein the organic molecule has a molecular weight less than 1000.

7. The method of claim 1, wherein the organic molecule has a molecular weight less than 500.

8. The method of claim 3, wherein the mammal is a human.

9. The method of claim 4, wherein the mammal is a human.

10. The method of claim 5, wherein the mammal is a human.

11. The method of claim 1, wherein the mammal in need of treatment for ocular angiogenesis has age-related macular degeneration.

12. The method of claim 1, wherein the mammal in need of treatment for ocular angiogenesis has choroidal neovascularization.

\* \* \* \* \*